(12) United States Patent
Govari (10) Patent No.: US 12,387,835 B2
(45) Date of Patent: *Aug. 12, 2025

(54) ASSESSING LESIONS FORMED IN AN ABLATION PROCEDURE

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/644,539

(22) Filed: Apr. 24, 2024

(65) Prior Publication Data

US 2024/0274265 A1 Aug. 15, 2024

Related U.S. Application Data

(63) Continuation of application No. 17/400,414, filed on Aug. 12, 2021, now Pat. No. 11,972,855.

(51) Int. Cl.
*G16H 20/40* (2018.01)
*A61B 18/00* (2006.01)
(Continued)

(52) U.S. Cl.
CPC ............. *G16H 20/40* (2018.01); *A61B 18/00* (2013.01); *A61B 34/25* (2016.02); *A61B 90/37* (2016.02); *G16H 30/40* (2018.01); *G16H 50/30* (2018.01); *G16H 50/50* (2018.01); *A61B 2018/00577* (2013.01); *A61B 2018/00839* (2013.01);
(Continued)

(58) Field of Classification Search
CPC ........ G16H 20/40; G16H 30/40; G16H 50/30; G16H 50/50; A61B 18/00; A61B 34/25; A61B 90/37; A61B 2018/00577; A61B 2018/00839; A61B 2018/00904; A61B 2090/364; A61B 5/0044; A61B 5/367; A61B 5/4848; A61B 5/7425; A61B 5/0036; A61B 18/1492; A61B 34/20; A61B 2018/00875; A61B 2018/00351; G06T 2210/41; G06T 19/00; G06T 7/11; G06T 2207/10132; G06T 2207/10088; G06T 2207/30048

See application file for complete search history.

(56) References Cited

U.S. PATENT DOCUMENTS 5,391,199 A 2/1995 Ben-Haim
6,239,724 B1 5/2001 Doron et al.
(Continued)

FOREIGN PATENT DOCUMENTS

WO 1996005768 A1 2/1996

OTHER PUBLICATIONS

Extended European Search Report dated Dec. 22, 2022, from corresponding European Application No. 22189867.9.

*Primary Examiner* — Xilin Guo (57) ABSTRACT

A method includes, receiving: (i) a selected three-dimensional (3D) section that has been ablated in a patient organ in accordance with a specified contour, and (ii) a dataset, which is indicative of a set of lesions formed during ablation of the selected 3D section. The selected 3D section is transformed into a two-dimensional (2D) map, and checking, on the 2D map, whether the set of lesions covers the specified contour.

20 Claims, 2 Drawing Sheets

(51) Int. Cl.
  *A61B 34/00*  (2016.01)
  *A61B 90/00*  (2016.01)
  *G16H 30/40*  (2018.01)
  *G16H 50/30*  (2018.01)
  *G16H 50/50*  (2018.01)

(52) U.S. Cl.
  CPC ............... *A61B 2018/00904* (2013.01); *A61B 2090/364* (2016.02)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim |
| 9,940,747 B2 | 4/2018 | Katz et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2016/0381256 A1* | 12/2016 | Aguirre-Valencia ........................ H04N 13/30 348/46 |
| 2018/0177467 A1 | 6/2018 | Katz et al. |
| 2020/0022649 A1* | 1/2020 | Rodriguez ........... A61B 5/4878 |
| 2020/0107877 A1 | 4/2020 | Koblish et al. |
| 2020/0245885 A1 | 8/2020 | Haeusser et al. |
| 2021/0093281 A1 | 4/2021 | Madabhushi et al. |

* cited by examiner

ASSESSING LESIONS FORMED IN AN ABLATION PROCEDURE

CROSS-REFERENCE TO RELATED APPLICATIONS

This application is a continuation of prior filed U.S. patent application Ser. No. 17/400,414, filed Aug. 12, 2021, now U.S. Pat. No. 11,972,855, the entire contents of which is hereby incorporated by reference as if set forth in full herein.

FIELD OF THE INVENTION

The present invention relates generally to graphical user interface (GUI) in medical systems, and particularly to methods and systems for assessing the shape and continuity of lesions formed in an ablation procedure of a blood vessel.

BACKGROUND

Various techniques for presenting and assessing lesions produced in tissue ablation, such as pulmonary vein (PV) isolation, have been published.

For example, U.S. Patent Application Publication 2020/0107877 describes systems and methods for facilitating assessment and convenient display of graphical output indicative of lesion formation and outputting data indicative of lesion formation to a 3D mapping system to display on a 3D model.

U.S. Patent Application Publication 2020/0245885 describes systems, devices, components and methods for detecting the locations of sources of cardiac rhythm disorders in a Patient's Heart.

SUMMARY

An embodiment of the present invention that is described herein provides a method including receiving: (i) a selected three-dimensional (3D) section that has been ablated in a patient organ in accordance with a specified contour, and (ii) a dataset, which is indicative of a set of lesions formed during ablation of the selected 3D section. The selected 3D section is transformed into a two-dimensional (2D) map, and checking, on the 2D map, whether the set of lesions covers the specified contour.

In some embodiments, checking on the 2D map includes receiving a starting point on the 2D map, and attempting to find a continuous ablated region that covers the specified contour starting from the received starting point. In another embodiments, the method includes presenting, over the 2D map, a set of symbols indicative of the set of lesions. In yet other embodiments, checking on the 2D map includes checking a continuity of the set of lesions, by checking that shapes corresponding to at least two adjacent symbols overlap one another.

In an embodiment, the set of symbols has a 2D graphical representation, and the method includes transforming the 2D map and the 2D graphical representation of the set of symbols, to a 3D map having the 2D graphical representation transformed to a 3D graphical representation and displayed over the 3D map. In another embodiment, the specified contour includes a closed loop, and checking on the 2D map includes verifying that the set of lesions covers the closed loop.

There is additionally provided, in accordance with an embodiment of the present invention, a system including an interface and a processor. The interface is configured to receive: (i) a selected three-dimensional (3D) section that has been ablated in a patient organ in accordance with a specified contour, and (ii) a dataset, which is indicative of a set of lesions formed during ablation of the selected 3D section. The processor is configured to: (i) transform the selected 3D section into a two-dimensional (2D) map, and (ii) check, on the 2D map, whether the set of lesions covers the specified contour.

The present invention will be more fully understood from the following detailed description of the embodiments thereof, taken together with the drawings in which:

DETAILED DESCRIPTION OF EMBODIMENTS

Overview

Ablation procedures typically aim to produce a lesion at a predefined location in tissue of a patient organ, so as to block the propagation of an electrophysiological (EP) wave, e.g., across the organ. After ablating the tissue, it is important to verify that the lesion is continuous, has the desired size and shape, and blocks the EP wave.

When ablating a tubular tissue, such as a pulmonary vein (PV) or another blood vessel connected to a patient heart, the assessment of the lesion properties and effectiveness is difficult. Specifically, a PV isolation procedure is intended to produce a continuous lesion having a ring shape along the inner circumference of the PV, so as to prevent or minimize arrhythmias in the patient heart. Therefore, the assessment and/or verification of the lesion properties and effectiveness in PV isolation is very important for the patient safety.

Embodiments of the present invention that are described hereinbelow provide improved techniques for checking whether a set of one or more lesions formed in tissue that has been ablated in accordance with a specified contour, covers (e.g., is aligned with) the specified contour. More specifically, checking whether in a PV isolation procedure, the set of lesions forms a continuous ring along the inner circumference of the PV.

In principle, it is possible to display the lesions on a three-dimensional (3D) anatomical map of the heart and PV(s) in question. However, in a 3D organ, and particularly in a tubular organ such as a PV or any other blood vessel, it is difficult to ascertain the continuity of the set of lesions formed along the inner circumference of the PV.

In some embodiments, a system comprising an interface, a processor and a display, is configured to assist a physician in checking whether, in a PV isolation procedure, the set of lesions forms a continuous ring along the inner circumference of the PV. The interface is configured to receive a 3D section of at least the PV in question, which has been ablated in accordance with a specified contour, and selected by the physician. The interface is further configured to receive a dataset, which is indicative of the set of lesions formed during ablation of the selected 3D section. The specified contour may be produced by the physician during the ablation planning, or may be any sort of continuous ring produced on the inner circumference of the PV.

In some embodiments, the processor is configured to transform the selected 3D section into a two-dimensional (2D) map, and to present over the 2D map, a set of symbols indicative of the set of lesions. The 2D map and set of symbols are displayed on the display or on any other suitable output device connected to the processor. In the present example, the processor has the parameters of the ablation (e.g., energy, duration and other parameters) at each ablation point, so that the set of symbols comprises a corresponding set of round (or elliptical) shapes, which is indicative of the area in which the lesion is formed at each point of the ablated tissue. In other embodiments, the processor may use any other suitable type of symbols indicative of the lesions.

In some embodiments, the interface is configured to receive from the physician a starting point on the 2D map, for starting to check whether the set of symbols (e.g., round shapes) covers the specified contour. In an embodiment, the processor is configured to attempt to find a continuous ablated region that covers the specified contour starting from the starting point received from the physician via the interface.

In other embodiments, the processor is configured to select the starting point automatically, without the physician, and/or to recommend a starting point to the physician.

In some embodiments, the processor is configured to check the continuity of the set of lesions by checking that shapes corresponding to at least two adjacent symbols (e.g., round shapes) overlap one another. In such embodiments, a string of overlapping round shapes that together produce a closed loop along the inner circumference of the PV, is indicative of a continuous lesion for obtaining the desired isolation of the PV and preventing the propagation of the aforementioned EP wave through the tissue of the PV.

In some embodiments, the processor is configured to detect a discontinuity in the lesion, and may produce an alarm and/or display the discontinuity to the physician (or any other user of the system). Moreover, based on the detected discontinuity, the processor is configured to recommend the physician to perform ablation at one or more additional points, so as to produce the continuous lesion and to obtain the desired EP isolation of the PV.

The disclosed techniques improve the quality of lesions produced in ablation procedures, and particularly, in ablation of blood vessels, such as pulmonary veins. Moreover, the disclosed techniques reduce the time required for verifying the outcome of the ablation procedure.

SYSTEM DESCRIPTION

Figure 1:
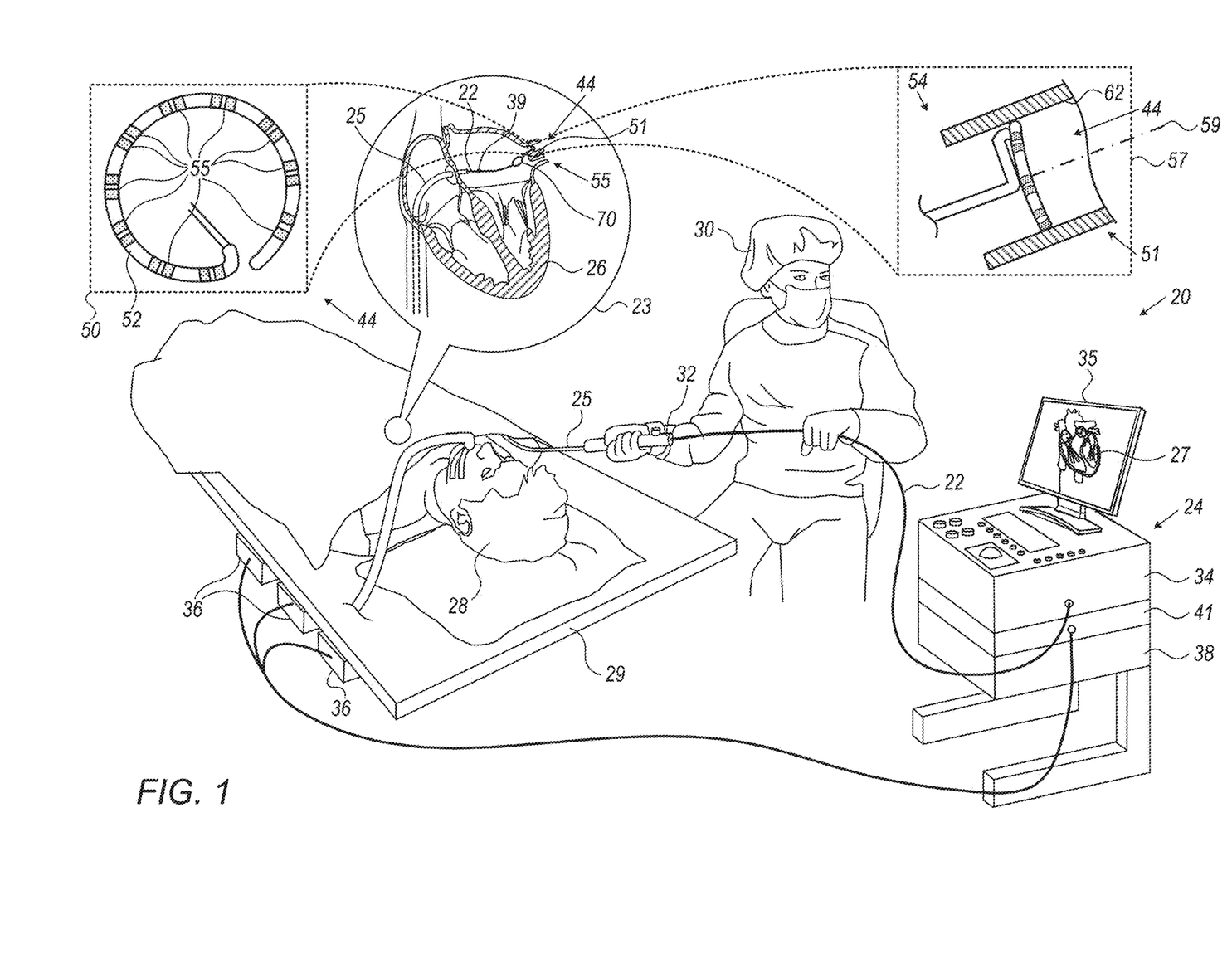
FIG. 1 is a schematic, pictorial illustration of a catheter-based tracking and ablation system, in accordance with an embodiment of the present invention.

FIG. 1 is a schematic, pictorial illustration of a catheter-based tracking and ablation system 20, in accordance with an embodiment of the present invention.

In some embodiments, system 20 comprises a catheter 22, in the present example a cardiac catheter, and a control console 24. In the embodiment described herein, catheter 22 may be used for any suitable therapeutic and/or diagnostic purposes, such as but not limited to sensing electrophysiological (EP) signals and performing electro-anatomical (EA) mapping of tissue of a heart 26 and for ablating tissue in question of heart 26, as will be described in detail below.

In some embodiments, console 24 comprises a processor 34, typically a general-purpose computer, with suitable front end and interface circuits for receiving signals via catheter 22 and for controlling the other components of system 20 described herein. In some embodiments, console 24 comprises an interface 38, which is configured to exchange signals between processor 34 and other entities of system 20. Console 24 further comprises a user display 35, which is configured to receive from processor 34 a map 27 of heart 26 and other graphical presentations, and to display map 27 and the graphical presentations. Additionally or alternatively, system 20 may comprise any other suitable output device, which is configured to display map 27 and other graphical elements described below to a user of system 20.

In some embodiments, map 27 may comprise any suitable type of a two-dimensional (2D) or a three-dimensional (3D) anatomical map produced using any suitable technique. For example, the anatomical map may be produced using an anatomical image produced by using a suitable medical imaging system, or using a fast anatomical mapping (FAM) techniques available in the CARTO™ system, produced by Biosense Webster Inc. (Irvine, Calif.), or using any other suitable technique, or using any suitable combination of the above.

In some embodiments, map 27 may comprise a 3D anatomical or electro-anatomical map, and after physician selects a section in map 27, processor 34 is configured to transform the selected section into a 2D map as will be described in detail in FIG. 2 below.

Reference is now made to an inset 23. In some embodiments, prior to performing an ablation procedure, a physician 30 inserts catheter 22 through the vasculature system of a patient 28 lying on a table 29, so as to perform EA mapping of tissue in question of heart 26.

In some embodiments, after performing the tissue ablation, physician 30 may place one or more electrodes 55 (described in detail below) of catheter 22 in contact with the tissue in question, so as to produce an EA map of the tissue that has been ablated. Subsequently, physician 30 uses the produced EA map for assessing the ablation impact and the condition of the ablated tissue.

In some embodiments, catheter 22 comprises a distal-end assembly having a balloon 70 and a lasso-shaped assembly, referred to herein as a lasso 44. In the present example, balloon 70 has ablation electrodes (not shown), which are configured to apply one or more ablation pulses to tissue, and lasso 44, which is fitted distally to balloon 70, has multiple sensing electrodes 55. In the context of the present disclosure and in the claims, the terms "electrodes" and "sensing electrodes" that are referred to electrodes 55 of lasso 44, are used interchangeably. Non-sensing electrodes, are referred to herein as "ablation electrodes" that are coupled to balloon 70, as will be described in detail below.

In some embodiments, in response to sensing EP signals, e.g., electrocardiogram (ECG) signals, in tissue of heart 26, each sensing electrode 55 is configured to produce one or more signals indicative of the sensed EP signals. In the example shown in inset 23, physician 30 inserts the distal-end assembly into a pulmonary vein (PV) 51 that transfers blood between heart 26 and the lungs (not shown) of patient 28. The ablation procedure typically requires at least three steps: (i) a first EA mapping using lasso 44, (ii) tissue ablation using the electrodes of balloon 70, and (iii) a second EA mapping using lasso 44. Both lasso 44 and balloon are expandable and are configured to place one or more of their electrodes in contact with tissue of PV 51. The steps are described in more detail below.

In some embodiments, based on the first EA mapping, physician 30 determines one or more locations intended for performing the tissue ablation. After ablating the tissue, physician 30 performs the second EA mapping for checking whether the ablation has obtained the desired outcome for treating the arrhythmia in patient heart 26.

Reference is now made to an inset 57 showing a side view of PV 51 and lasso 44 inserted along a longitudinal axis 59 of PV 51. Note that balloon 70, which is configured to ablate the tissue of PV 51, and is coupled to catheter 22 proximally to lasso 44, is not shown in inset 57.

In some embodiments, processor 34 receives, via interface 38 or directly, a dataset comprising, inter alia: (i) a contour of the tissue ablation that is typically specified by physician 30, (ii) the position of each ablation electrode of balloon 70 placed in contact with the tissue (using a position tracking system described below) in accordance with the specified contour, and (iii) selected parameters of the ablation pulses applied to the tissue during the ablation. The selected parameters may comprise energy of the ablation pulse(s), duration of ablation pulse(s), and contact force applied between each of the ablation electrodes and the ablated tissue.

In some embodiments, based on the dataset, processor 34 is configured to check, and optionally present, whether the set of lesions covers the contour specified by physician 30, as will be described in more detail in FIGS. 2 and 3 below.

In some embodiments, during the ablation procedure physician 30 inserts lasso 44 through an ostium 54 of PV 51, so as to carry out the sensing and tissue ablation activities described above. Physician 30 moves lasso 44 along longitudinal axis 59 and when obtaining the desired position, physician 30 using a manipulator 32 for expanding lasso 44 so as to place one or more electrodes 55 of lasso 44 in contact with the surface of an inner wall section 62 of PV 51. In the context of the present disclosure, the term inner wall section refers to an annular section that extends along longitudinal axis 59 of the inner wall of PV 51.

Reference is now made to an inset 50, which is a top-view of lasso 44. In some embodiments, lasso 44 comprises (i) a flexible arm 52, which is controlled by manipulator 32 and is configured to: (a) expand so as to conform to the surface of inner wall section 62 of PV 51, and (b) collapse so as to move lasso 44 within heart 26 and the vasculature of patient 28, and (ii) multiple electrodes 55 coupled to arm 52 and configured to sense the EP signals (in the present example) and/or to ablate the surface of inner wall section 62 of PV 51. Note that electrodes 55 are configured for sensing the EP signals, and the electrodes (not shown) of balloon 70 are configured for applying ablation pulses to tissue of inner wall section 62 of PV 51.

Reference is now made back to inset 23. In some embodiments, physician 30 inserts catheter 22 through a sheath 25, and uses manipulator 32 for manipulating catheter 22 and for positioning lasso 44 and the distal end of sheath 25 in close proximity to ostium 54 of PV 51. Subsequently, physician 30 uses manipulator 32 to retract sheath 25, so as to expose and move balloon 70 and lasso 44 into a desired position within PV 51. During the first EA mapping, physician 30 applies manipulator 32 for expanding arm 52 so that at least some of electrodes 55 are placed in contact with the surface of inner wall section 62 of PV 51. Note that the positioning of balloon 70 and lasso 44 within PV 51, is carried out using a position tracking system, which is described in detail below.

In some embodiments, after positioning and expanding lasso 44 at the desired position(s) in PV 51, physician 30 performs the first EA mapping before planning and performing the tissue ablation. Note that based on the first EA mapping, processor 34 may produce and display a first EA map on display 35, and based on the first EA map, physician 30 may define the ablation site(s) along inner wall section 62 of PV 51. In the present example, the ablation procedure comprises a PV isolation procedure in which inner wall section 62 tissue of PV 51 is ablated by the electrodes of balloon 70, at a target position defined by physician 30 based on the first EA mapping described above. The PV isolation is intended to form a lesion in the tissue, so as to prevent or minimize (e.g., to a level below a predefined threshold) the propagation of EP waves through and/or along the tissue of inner wall section 62 of PV 51. In some example embodiments, lasso 44 is operated for both mapping and ablating. Optionally, same electrodes 55 are configured to alternate between mapping and ablating. Optionally, lasso 44 includes one or more dedicated electrodes for ablating, e.g., one or more electrodes other than electrodes 55. Optionally, when lasso 44 is operated for both mapping and ablating, balloon 70 is not required.

In other words, the term "PV isolation" refers to blockage of EP waves from propagating through and/or along the walls of PV 51.

In some embodiments, in the second EA mapping, which is typically carried out after ablating the tissue, physician 30 moves lasso 44 along longitudinal axis 59 and selects one or more positions in which he/she expands lasso 44 for sensing EP signals at the ablation site and typically also at additional positions along PV 51. In the present example, the ablation pulses are applied to tissue of inner wall section 62, located in close proximity to or directly at ostium 54, and the second EA mapping is carried out at multiple positions between ostium 54 and about 2 cm into PV 51, along longitudinal axis 59.

In some embodiments, when performing the second EA mapping, physician 30 checks one or more quality measures of the ablated PV 51. One example quality measure may comprise an amplitude of an EP signal (e.g., voltage) sensed by a respective electrode 55. The sensed EP signal is indicative of either the propagation or blockage of EP waves at the ablated site of PV 51. In other words, the second EA mapping checks whether the ablation obtained the desired electrical isolation of PV 51.

In some embodiments, in case the ablation obtained the desired level of PV isolation, physician 30 retracts lasso 44 out of PV 51, inserts lasso 44 into sheath 25, and concludes the ablation procedure by retracting catheter 22 out of the body of patient 28. In case the amplitude of the sensed EP voltage is larger than a predefined threshold at one or more positions along inner wall section 62, physician 30 may have to conduct an additional ablation session, so as to obtain the desired level of PV isolation, measured by the amplitude of the sensed EP voltage, or by any other suitable measured parameter. After conducting the tissue ablation using balloon 70, physician 30 typically repeats the second EA mapping, so as to confirm that the desired level of PV isolation has been obtained.

Reference is now made back to the general view of FIG. 1. In some embodiments, the proximal end of catheter 22 is connected, inter alia, to interface circuits (not shown), so as to transfer and store the EP sensed signals to a memory (not shown) of console 24, so that processor 34 can use the stored EP signals for performing the EA mapping. In some embodiments, based on the sensed EP signals, processor 34 is configured to present the aforementioned 2D and/or 3D map(s) to physician 30 (e.g., on display 35). Moreover, processor 34 is configured to present on the 2D or 3D map, a graphical presentation indicative of the one or more quality measures described above and/or another graphical presentation indicative of other parameters related to one or more lesions formed in the tissue during the ablation procedure. Embodiment of example graphical presentations are depicted in more detail in FIG. 2 below.

In the context of the present disclosure and in the claims, the terms "about" or "approximately" for any numerical values or ranges indicate a suitable dimensional tolerance that allows the part or collection of components to function for its intended purpose as described herein.

In other embodiments, catheter 22 may have an apparatus other than balloon 70, for ablating tissue at the one or more desired position(s) along inner wall section 62, so as to carry out the aforementioned PV isolation. Additionally or alternatively, physician 30 may use a separate catheter for ablation tissue of PV 51.

In some embodiments, the position of the distal-end assembly in the heart cavity and along PV 51 is measured using a position sensor 39 of a magnetic position tracking system, which may be coupled to the distal-end assembly at any suitable position. In the present example, console 24 comprises a driver circuit 41, which is configured to drive magnetic field generators 36 placed at known positions external to patient 28 lying on table 29, e.g., below the patient's torso. As described above, position sensor 39 is coupled to the distal end, and is configured to generate position signals in response to sensed external magnetic fields from field generators 36. The position signals are indicative of the position the distal end of catheter 22 in the coordinate system of the position tracking system.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178b820A1, whose disclosures are all incorporated herein by reference.

In some embodiments, the coordinate system of the position tracking system are registered with the coordinate systems of system 20 and map 27, so that processor 34 is configured to display, the position of lasso 44 and/or balloon 70 of the distal-end assembly, over the anatomical or EA map (e.g., map 27).

In some embodiments, processor 34 is assembled in a suitable computer, and typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

In other embodiments, system 20 may have, instead of or in addition to lasso 44 and/or balloon 70, any other suitable sort of one or more catheters, which are configured to carry out the sensing and ablation described above, in PV 51 or in any other sort of a blood vessel or in any other organ or a section of an organ having a tubular shape or any other 3D shape.

Figure 2:
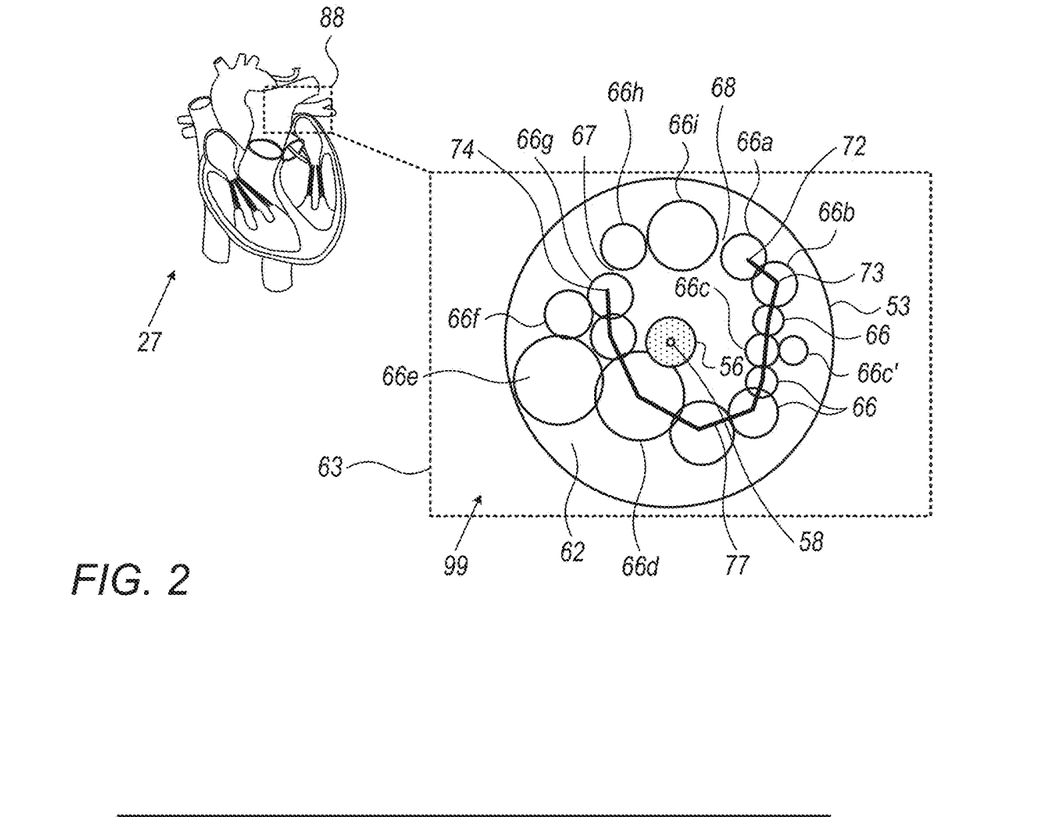
FIG. 2 is a schematic, pictorial illustration of a selected three-dimensional (3D) section in a patient heart, which is presented in a two-dimensional (2D) map and a set of lesions and a specified contour presented over the 2D map, in accordance with an embodiment of the present invention.

Presenting and Checking Geometrical Properties of a Set of Lesions Formed in Ablated Tissue FIG. 2 is a schematic, pictorial illustration of a selected three-dimensional (3D) section 88 in patient heart 26, which is presented in a two-dimensional (2D) map 99, in accordance with an embodiment of the present invention.

In the present example, 3D section 88 comprises PV 51 of heart 26, which is shown in 3D map 27 displayed on display 35. In some embodiments, in response to the selection of 3D section 88 by physician 30 (or by any other user of system 20), processor 34 is configured to transform 3D section 88 into 2D map 99. 2D map 99 may be a flattened representation of an inner wall of PV 51. Optionally, 2D map may be a flattened representation of an inner wall of any other generally cylindrically shaped vessel that is being treated with ablation. In such embodiments, 2D map 99 comprises a sectional view of PV 51 at a position selected by physician 30 along longitudinal axis 59 of PV 51.

In some embodiments, 2D map 99 comprises a polar coordinate system having an origin 58, which is indicative of longitudinal axis 59 of PV 51. In such embodiments, ostium 54 is represented by a circle 53, and a circle 56 represents a second position located at about 2 cm from ostium 54, into PV 51 along longitudinal axis 59, as described in FIG. 1 above.

In other embodiments, at least one of circles 53 and 56 may have, instead of a circular-shape, a shape of an ellipse or any other suitable shape.

In some embodiments, the tissue of inner wall section 62 of PV 51 is represented by a doughnut-shaped element defined between circles 53 and 56, e.g., a section of a PV inner wall extending along longitudinal axis 59 from ostium 54 to about 2 cm from ostium 54. Note that the polar coordinate system enables a 2D presentation of the 3D shape of PV 51 in 2D map 99, and the distance from the origin 58, also referred to herein as a pole, along the polar axis is indicative of a position of any element described herein on inner wall section 62, along longitudinal axis 59 of PV 51, e.g., the polar axis defines a position along a length of PV 51.

In the present example, 2D map 99 represents a view from a cavity (e.g., a left atrium) of heart 26, into PV 51, so that circle 53 (representing ostium 54) appears larger than circle 56, which is positioned, along longitudinal axis 59, about 2 cm into PV 51.

In other embodiments, physician 30 may select, for analysis, any other position of 3D section 88 along longitudinal axis 59 of PV 51. In such embodiments, at least one of circles 53 and 56 may refer to any other respective position along longitudinal axis 59 of PV 51.

In some embodiments, before ablating the tissue of PV 51, physician 30 defined, e.g., by drawing on map 27, a specified contour (not shown on map 27, but shown and described below over 2D map 99) of the ablation at a selected position along longitudinal axis 59 of PV 51. In some embodiments, during the ablation, physician 30 inflates balloon 70 for ablating inner wall section 62 of the tissue of PV 51 at one or more locations, as described in detail in FIG. 1 above.

In some embodiments, after performing the tissue ablation, physician 30 selects 3D section 88 for analysis, and processor 34 transforms 3D section 88 into 2D map 99, and presents 2D map 99 on display 35.

Reference is now made to an inset 63, which shows 2D map 99 that may be displayed on display 35.

In some embodiments, processor 34 receives, e.g., via interface 38, a dataset which is indicative of a set of lesions 66 formed during ablation of the selected section of PV 51, and a specified contour 77, which processor 34 presents over 2D map 99. In the example of FIG. 2, the term lesion 66 refers to all the lesions starting with numeral 66 (e.g., lesions 66a, 66b, 66c etc.). Note that contour 77 is based on the contour specified by physician 30, as described above, and a 2D projection thereof is presented over 2D map 99.

Note that circle 56 is filled with a dotted texture solely for the sake of graphically differentiating between lesions 66 and the inner circumference of PV 51 at a given position along longitudinal axis 59, which is represented by circle 56. It will be understood that PV 51 is hollow and extends along longitudinal axis 59, so that the dotted texture does not represent any blockage or any sort of material other than blood flowing through PV 51.

As described in FIG. 1 above, the dataset comprises, inter alia, parameters of the ablation pulses applied to the tissue by the electrodes of balloon 70. In some embodiments, based on the parameters, processor 34 is configured to estimate the size (e.g., diameter) of each lesion 66, and to present a set of symbols indicative of the set of lesions 66 over 2D map 99. Processor 34 is further configured to check whether one or more of lesions 66 cover contour 77. In the context of the present disclosure and in the claims, the term "cover" refers to an overlap between a given lesion 66 and a section of contour 77. Moreover, processor 34 is configured to check whether the areas of two or more adjacent lesions 66 (e.g., lesions 66 positioned along contour 77) overlap one another, so as to produce a continuous lesion (e.g., along contour 77), as described herein.

In some embodiments, physician 30 may use processor 34 for checking the continuity of lesions 66 formed along contour 77 using any suitable technique. In such embodiments, physician 30 may select an ablation point 72 for processor 34 to start the lesion continuity check. Subsequently, processor 34 checks for an ablation point that has ablated tissue in contact with the selected point (e.g., ablation point 72). In the present example, lesion 66a is positioned on and therefore covers ablation point 72. Note that processor 34 receives (e.g., via interface 38) the position of each ablation point on inner wall section 62 of PV 51, based on the coordinate system of the position tracking system. Moreover, processor 34 holds the ablation parameters defined for each ablation point along contour 77, which determine the size (e.g., diameter) of each lesion 66 presented over 2D map 99 of PV 51.

In some embodiments, processor 34 is configured to continue this process for each point along contour 77 until returning to the initial point (e.g., point 72), or until processor 34 can no longer find a valid ablation point.

In the present example, after identifying that lesion 66a covers point 72, processor 34 proceeds along contour 77 to point 73 and identifies lesion 66b that (i) covers point 73, and (ii) whose area overlaps with the area of lesion 66a. Processor 34 continues the check by moving along contour 77 and checks that lesions 66 cover contour 77 and adjacent lesions 66 overlap one another. In the present example, processor 34 moves clockwise along contour 77 and identifies that lesions 66, 66c, 66e, and 66g are all covering contour 77 and overlap to for a continuous lesion along contour 77. However, processor 34 also identifies that the lesion formed along inner wall section 62 cannot obtain full PV isolation.

In other embodiments, processor 34 may check the continuity of lesions 66 formed along inner wall section 62 regardless the ablation contour produced by physician 30 during the planning of the ablation procedure. In such embodiments, processor 34 is configured to produce a continuous line between adjacent lesions 66 overlapping one another. For example, the line representing contour 77 may comprise a line produced by processor 34 for representing the continuity of the area covered by lesions 66 along inner wall section 62 of PV 51. As shown in inset 63, the line is continuous when moving clockwise between points 72 and 74, but is disconnected between lesions 66g and 66a.

In such embodiments, processor 34 is configured to identify that the areas of: (i) lesions 66g and 66h are not overlapping one another, (ii) lesions 66i and 66a are not overlapping one another, and (iii) lesions 66h and 66i are barely touching one another. Thus no continuous lesion has been formed along inner wall section 62, and therefore, the EP wave can propagate though the tissue of PV 51. Moreover, processor 34 is configured to identify that lesion 66c' overlaps with lesion 66c but is disconnected from all other lesions 66 produced during the ablation procedure. Similarly, processor 34 is configured to identify that lesions 66e and 66f do form a second and longer continuous line between lesions 66d and 66g.

In some embodiments, processor 34 identifies: (i) a gap 67 between lesions 66g and 66h, (ii) a gap 68 between lesions 66i and 66a, and (iii) insufficient or lack of overlap between lesions 66i and 66h. In other words, processor 34 identifies discontinuity between these pairs of lesions. In such embodiments, processor 34 is configured to provide physician 30 with a recommendation of how to obtain a continuous ring of lesions 66 along inner wall section 62 of PV 51. For example, processor 34 may recommend to perform ablation at gaps 67 and 68, and between lesions 66i and 66h, so as to obtain full isolation of PV 51, i.e., to block the EP wave from progressing through the tissue of PV 51.

In some embodiments, compared to the presentation of 3D section 88, 2D map 99 provides physician 30 with an improved visualization of the lesions formed during the ablation procedure, because checking the continuity is typically easier in a 2D map compared to a 3D map. In other embodiments, after presenting 2D map 99, processor 34 is configured to transform 2D map 99 into a 3D map (not shown), and to implement the 3D map in section 88. Moreover, after identifying the lesion discontinuity, and performing additional ablations at gaps 67 and 68, and between lesions 66i and 66h, processor 34 is configured to produce a revised 2D map 99 that visualizes the formation of a continuous ring made from a set of lesions 66 in inner wall section 62. Subsequently, processor 34 is configured to transform the revised 2D map 99 into a 3D map, and to implement the new 3D in lieu of 3D section 88. The formation of the revised 2D and 3D maps may be carried out automatically or in response to a request from physician 30 or any other user of system 20.

In alternative embodiments, processor 34 is configured to check: (i) whether one or more of lesions 66 cover contour 77, and (ii) the overlap between areas of adjacent lesions 66 covering contour 77, without displaying lesions 66 and/or contour 77 over 2D map 99. For example, processor 34 may issue a pop-up alarm in case: (i) contour 77 is not fully covered by lesions 66, and/or (ii) the areas of two or more adjacent lesions 66, which are positioned along contour 77, are not overlapping one another. In such embodiments, processor 34 is configured to show, in the graphical user interface (GUI) presented on display 35, an option to hide or display lesions 66 and/or contour 77 over 2D map 99.

Figure 3:
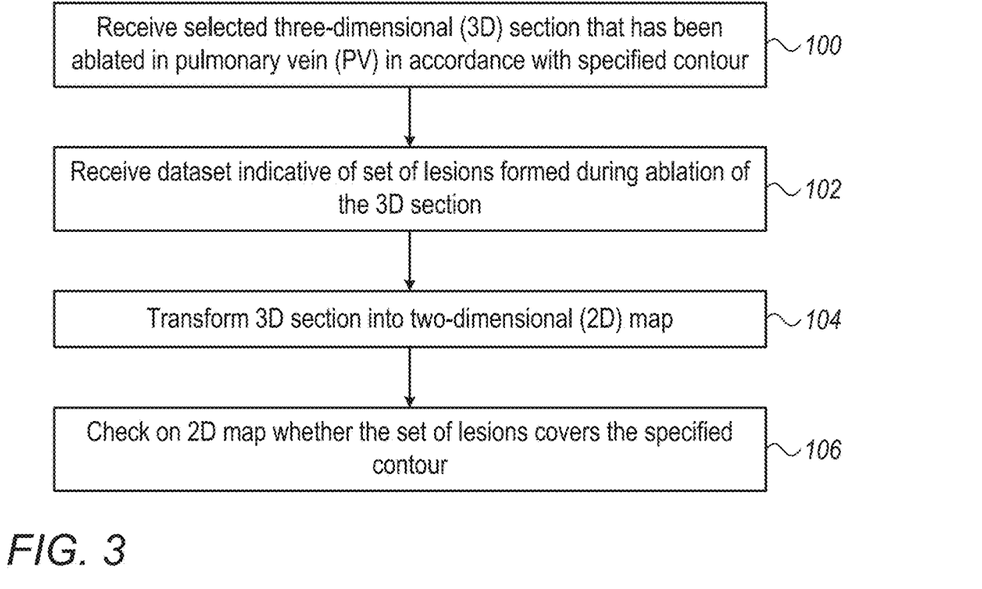
FIG. 3 is a flow chart that schematically illustrates a method for checking whether a set of lesions that is formed in tissue ablation, covers a specified contour, in accordance with an embodiment of the present invention.

FIG. 3 is a flow chart that schematically illustrates a method for checking whether a set of lesions 66 that is formed in tissue ablation, covers contour 77, in accordance with an embodiment of the present invention. The method begins at a 3D section receiving step 100, with processor 34 receiving (e.g., via interface 38) 3D section 88 of PV 51 that has been ablated in accordance with a specified contour 77 defined by physician 30, as described in FIG. 2 above.

At a dataset receiving step 102, processor receives (e.g., via interface 38) a dataset indicative of a set of lesions (e.g., lesions 66 shown in FIG. 2 above) formed during the ablation on 3D section 88 of PV 51.

At a transformation step 104, processor 34 transforms selected 3D section 88 into 2D map 99 as shown and depicted in detail in inset 63 of FIG. 3 above. At a lesion checking step 106 that concludes the method, processor 34 checks whether the set of lesions 66 covers specified contour 77.

In some embodiments, processor 34 is configured to present a set of symbols indicative of the set of lesions 66 over 2D map 99. In the example of FIG. 2, the set of symbols comprises a set of circles, so that physician 30 can check whether or not the areas of the circles overlap one another. Processor 34 is further configured to present contour 77 as graphical object (e.g., a line) over 2D map 99. Moreover, processor 34 is configured to: (i) receive (e.g., via interface 38) from physician 34 a starting point (e.g., point 72) on 2D map, and (ii) attempt to find a continuous ablated region that covers contour 77 starting from the received starting point (e.g., point 72), as described in FIG. 2 above.

In some embodiments, processor 34 is configured to check the continuity of the ablated region that covers contour 77, by checking that shapes corresponding to at least two adjacent symbols that represent at least two lesions 66, respectively, overlap one another.

In some embodiments, contour 77 may comprise a closed loop, and processor 34 is configured to assess the shape of the set of lesions 66, and to verify that the set of lesions 66 covers the entire closed loop of contour 77 that was specified by physician 30 before or after applying the ablation pulses to the tissue in question, as described in FIG. 2 above.

In the context of the present disclosure and in the claims, the terms "assessing," "checking" and "verifying," are used interchangeably and refer to the ability of processor 34 to validate whether the set of lesions described in FIG. 2 above, form a continuous closed loop in inner wall section 62 of PV 51. Moreover, these terms may also refer to the ability of a user of the system (e.g., physician 30) to validate the continuity and shape of the lesions relative to the aforementioned specified contour, based on a GUI presented by processor 34 on display 35.

Although the embodiments described herein mainly address pulmonary vein (PV) isolation procedures carried out by ablating tissue of a PV, the methods and systems described herein can also be used in other applications, such as in ablation of any blood vessel or another suitable type of a three-dimensional organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method, comprising:
receiving: (i) three-dimensional (3D) data indicative of a selected 3D section that has been ablated in a patient organ, and (ii) a dataset indicative of a set of lesions formed during ablation of the selected 3D section;
transforming the selected 3D data into a two-dimensional (2D) map by generating a flattened representation of the selected 3D section; and
determining whether the set of lesions form a continuous lesion along a specified portion of the patient organ represented on the generated 2D map of the selected 3D section.

2. The method according to claim 1 further comprising, in response to determining that the set of lesions does not form a continuous lesion, identifying one or more options for forming a continuous lesion along the specified portion.

3. The method according to claim 2 further comprising identifying a longest possible path of the one or more options for forming a continuous lesion along the specified portion.

4. The method according to claim 1 further comprising, in response to determining that the set of lesions does not form a continuous lesion, providing a recommendation on how to obtain a continuous lesion along the specified portion.

5. The method according to claim 1, wherein the selected 3D section comprises an inner wall of a cylindrically-shaped vessel.

6. The method according to claim 1, wherein determining whether the set of lesions form a continuous lesion along the specified portion comprises receiving a starting point on the 2D map, and attempting to find a continuous ablated region that covers the specified portion starting from the received starting point.

7. The method according to claim 1, wherein determining whether the set of lesions form a continuous lesion along the specified portion comprises automatically identifying a starting point on the 2D map, and attempting to find a continuous ablated region that covers the specified portion starting from the received starting point.

8. The method according to claim 1, and comprising presenting, over the 2D map, a set of symbols indicative of the set of lesions.

9. The method according to claim 8, wherein determining whether the set of lesions form a continuous lesion along the specified portion comprises checking a continuity of the set of lesions, by checking that shapes corresponding to at least two adjacent symbols overlap one another.

10. The method according to claim 9, wherein the set of symbols comprises a 2D graphical representation, the method further comprising transforming the 2D map and the 2D graphical representation of the set of symbols, to a 3D map having the 2D graphical representation transformed to a 3D graphical representation and displayed over the 3D map.

11. The method according to claim 1, wherein the specified portion of the patient organ comprises a closed loop, and wherein determining whether the set of lesions form a continuous lesion along the specified portion comprises verifying that the set of lesions covers the closed loop.

12. A method, comprising:
receiving: (i) three-dimensional (3D) data indicative of a selected 3D section that has been ablated in a patient organ, and (ii) a dataset indicative of a set of lesions formed during ablation of the selected 3D section;
transforming the selected 3D data into a two-dimensional (2D) map by generating a flattened representation of the selected 3D section; and
identifying, among the set of lesions, a discontinuity in the set of lesions along a specified portion of the patient organ represented on the generated 2D map of the selected 3D section.

13. The method according to claim 12, wherein the selected 3D section comprises an inner wall of a cylindrically-shaped vessel.

14. The method according to claim 12 further comprising providing a recommendation on how to obtain a continuous lesion along the specified portion.

15. The method according to claim 14, wherein providing a recommendation on how to obtain a continuous lesion along the specified portion comprises identifying one or more locations along the specified portion to perform ablation.

16. The method according to claim 12 further comprising, identifying one or more options for forming a continuous lesion along the specified portion.

17. The method according to claim 13 further comprising identifying a longest possible path of the one or more options for forming a continuous lesion along the specified portion.

18. The method according to claim 16, wherein identifying one or more options for forming a continuous lesion along the specified portion comprises receiving a starting point on the 2D map, and attempting to find a continuous ablated region that covers the specified portion starting from the received starting point.

19. The method according to claim 16, wherein identifying one or more options for forming a continuous lesion along the specified portion comprises automatically identifying a starting point on the 2D map, and attempting to find a continuous ablated region that covers the specified portion starting from the received starting point.

20. The method according to claim 12, wherein identifying the discontinuity in the set of lesions along the specified portion of the patient organ comprises checking that shapes corresponding to at least two adjacent symbols indicative of the set of lesions overlap one another.

* * * * *